United States Patent
Kirwan, Jr.

(10) Patent No.: US 6,174,310 B1
(45) Date of Patent: Jan. 16, 2001

(54) BIPOLAR COAXIAL COAGULATOR HAVING OFFSET CONNECTOR PIN

(75) Inventor: Lawrence T. Kirwan, Jr., Pembroke, MA (US)

(73) Assignee: Kirwan Surgical Products, Inc., Marshfield, MA (US)

(*) Notice: Under 35 U.S.C. 154(b), the term of this patent shall be extended for 0 days.

(21) Appl. No.: 09/316,554

(22) Filed: May 24, 1999

(51) Int. Cl.⁷ ............................................. A61B 18/18
(52) U.S. Cl. ................................... 606/50; 606/49
(58) Field of Search ....................... 606/41, 42, 45–50

(56) References Cited

U.S. PATENT DOCUMENTS

| 4,548,207 | 10/1985 | Reimels . | |
|---|---|---|---|
| 4,674,499 | * 6/1987 | Pao | 606/50 |
| 4,805,616 | * 2/1989 | Pao | 606/50 |
| 5,089,002 | 2/1992 | Kirwan, Jr. . | |
| 5,277,696 | * 1/1994 | Hagen | 606/49 |
| 5,281,216 | * 1/1994 | Klicek | 606/42 |
| 5,290,285 | * 3/1994 | Kirwan, Jr. | 606/50 |
| 5,814,043 | * 9/1998 | Shapeton | 606/48 |

OTHER PUBLICATIONS

8ᵗʰ Edition of the Metals Handbook, vol 4, Forming (pp. 349–352).

* cited by examiner

*Primary Examiner*—Michael Peffley
(74) *Attorney, Agent, or Firm*—Wingarten, Schurgin, Gagnebin & Hayes LLP

(57) ABSTRACT

A bipolar coagulator includes a connector pin having an offset therein to provide a strong electrical connection between the pin and the conductor. The bipolar coagulator comprises an insulative housing extending along a longitudinal axis from a tip to a connector end. A coaxial conductor having an inner conductor and an outer conductor is disposed within the housing along the longitudinal axis of the housing. The inner conductor includes a terminal portion that protrudes from the outer conductor and has an offset therein to space the terminal portion from the longitudinal axis of the housing. A first connector pin is electrically coupled to the terminal portion of the inner conductor. A second connector pin is electrically coupled to the outer conductor along the longitudinal axis of the housing. The second connector includes an offset therein to space the pin portion from the longitudinal axis of the housing and from the first connector pin.

9 Claims, 4 Drawing Sheets

BIPOLAR COAXIAL COAGULATOR HAVING OFFSET CONNECTOR PIN

CROSS REFERENCE TO RELATED APPLICATIONS

N/A

STATEMENT REGARDING FEDERALLY SPONSORED RESEARCH OR DEVELOPMENT

N/A

BACKGROUND OF THE INVENTION

Bipolar coaxial coagulators are used to coagulate tissue during, for example, eye surgery. A bipolar coaxial coagulator includes coaxial inner and outer conductors separated by an insulating material. A pair of connector pins is electrically coupled to the inner and outer conductors and extends from the housing for connection to a socket of an electrosurgical generator.

A difficulty with bipolar coaxial coagulators has been to electrically connect the coaxial conductors to the spaced connector pins. An exemplary bipolar coagulator is illustrated in U.S. Pat. No. 5,089,002. In this device, the outer conductor includes an offset portion at one end. An opening is ground in the bend of the offset portion. The inner conductor is inserted through this opening. The inner conductor also includes an offset portion at one end. Connector pins are attached to the inner and outer conductors near the offset portions. It has been found, however, that the opening ground in the bend of the offset portion of the outer conductor creates a weakened section in the outer conductor, which may lead to premature failure of the coagulator.

BRIEF SUMMARY OF THE INVENTION

The present invention provides a bipolar coagulator with a connector pin having an offset therein. The offset connector pin provides a strong electrical connection between the pin and the conductor. Additionally, the offset connector pin can be manufactured with fewer production operations.

More particularly, the bipolar coagulator comprises an insulative housing comprising a single, unitary body extending along a longitudinal axis from a tip to a connector end. A coaxial conductor is disposed within the insulative housing along the longitudinal axis of the housing. The coaxial conductor comprises an inner conductor, an outer conductor coaxial with the inner conductor, and an insulating material concentrically disposed between the inner conductor and the outer conductor. The coaxial conductor protrudes from the tip of the housing.

The inner conductor includes a terminal portion protruding from the outer conductor within the connector end of the housing. The terminal portion includes an offset therein to space the terminal portion from the longitudinal axis of the housing. A single-piece, first connector pin, comprising a sleeve portion and a pin portion, is electrically coupled to the terminal portion of the inner conductor within the connector end of the housing. The pin portion protrudes from the connector end of the housing for connection to a socket of an electrosurgical generator.

A single-piece, second connector pin is electrically coupled to the outer conductor within the connector end of the housing along the longitudinal axis of the housing. The second connector includes a sleeve portion coupled to the outer conductor and a pin portion having an offset therein to space the pin portion from the longitudinal axis of the housing and from the first connector pin.

BRIEF DESCRIPTION OF THE DRAWINGS

The invention will be more fully understood from the following detailed description taken in conjunction with the accompanying drawings in which.

DETAILED DESCRIPTION OF THE INVENTION

Figure 1:
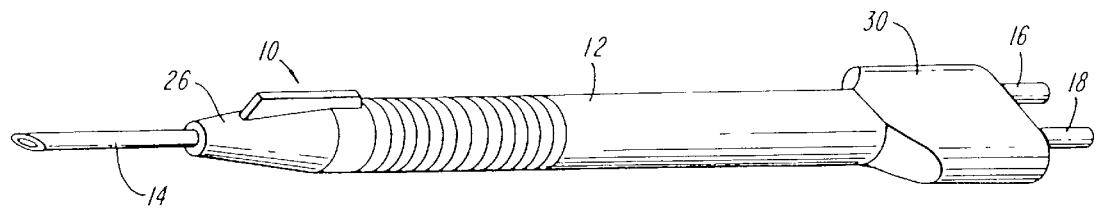
FIG. 1 is an isometric view of a bipolar coagulator according to the present invention.
Figure 2:
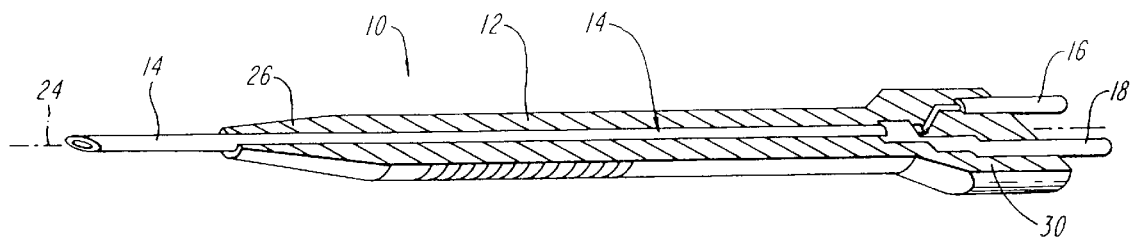
FIG. 2 is a cross-sectional view of the bipolar coagulator of FIG. 1.
Figure 3:
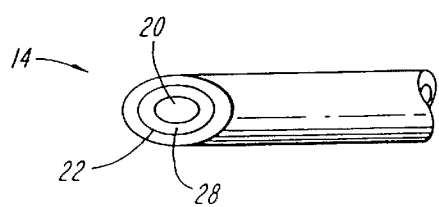
FIG. 3 is a partial view of the tip of the coaxial conductor of the bipolar coagulator of FIG. 1.
Figure 4:
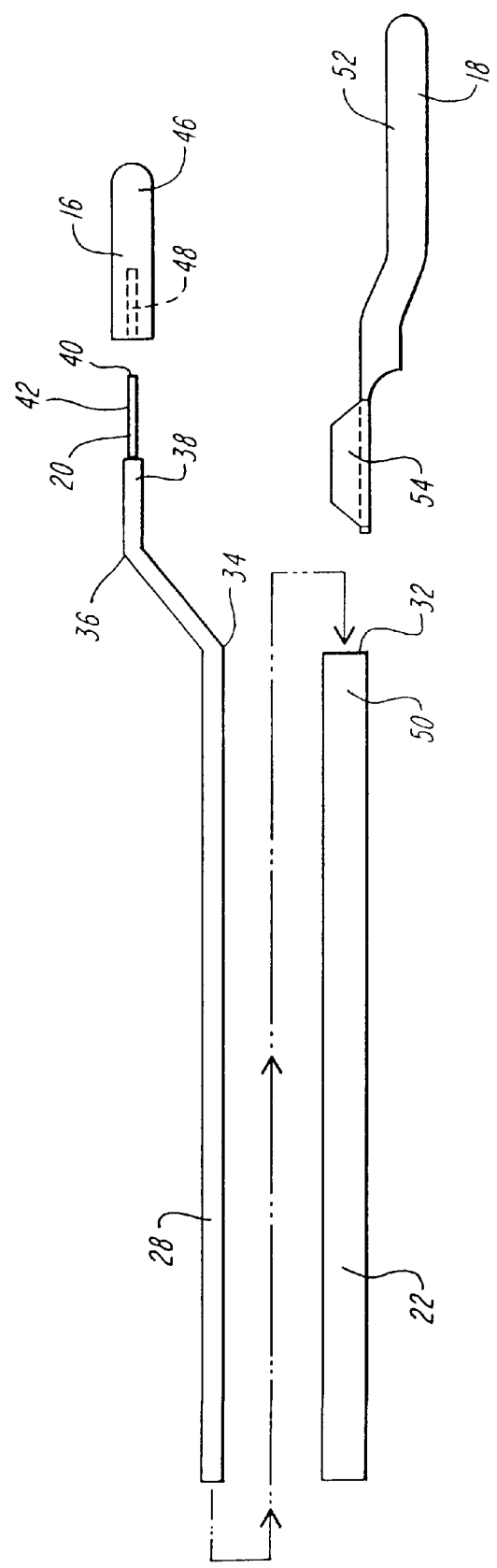
FIG. 4 is an exploded view of the coaxial conductor and first and second connector pins of the bipolar coagulator of FIG. 1.
Figure 5:
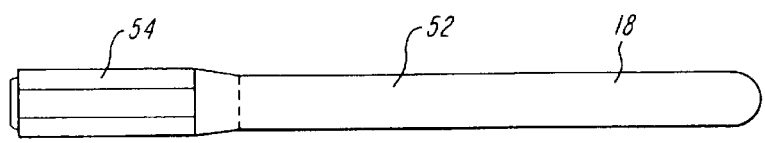
FIG. 5 is a top plan view of the second connector pin of FIG. 4.
Figure 7:
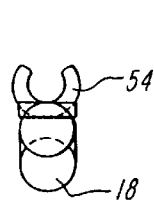
FIG. 7 is an end view of the second connector pin of FIG. 5.
Figure 6:
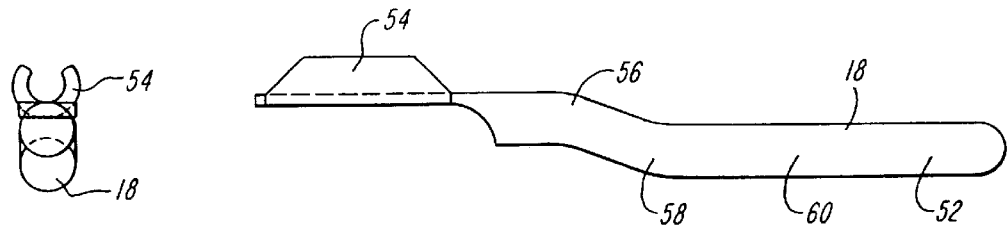
FIG. 6 is a side view of the second connector pin of FIG. 5.

Referring to FIG. 1, a bipolar coaxial coagulator 10 according to the present invention includes a housing 12, a coaxial conductor 14, and first and second connector pins 16, 18. The connector pins 16, 18 connect to a socket of an electrosurgicial generator (not shown), as is known in the art. The coaxial conductor 14 comprises an inner conductor 20 and an outer conductor 22 that extend along a longitudinal axis 24 of the housing 12 and protrude from the tip 26 of the housing. An insulating material 28 separates the inner conductor 20 and the outer conductor 22. The inner conductor and outer conductor are formed of any suitable conductive material, such as stainless steel, pure nickel or any other suitable conductive material.

At the connector end 30 of the housing 12, the inner conductor 20, concentrically surrounded by the insulating material 28, extends beyond the end 32 of the outer conductor 22. The inner conductor and insulating material are bent at first and second bends 34, 36 to form an offset 38 from the longitudinal axis 24 of the housing 12. The insulating material 26 terminates before the end 40 of the inner conductor 20 to expose a terminal portion 42 of the inner conductor.

The first connector pin 16 is electrically coupled to the terminal portion of the inner conductor. The first connector pin is formed from a single piece of a suitable electrically conductive material, such as brass, as is known in the art. The pin 16 includes a pin portion 46 and a sleeve portion 48. The pin portion 46 is typically solid and extends from the housing for a distance suitable for connection to the socket of the electrosurgical generator. The offset 38 of the inner conductor 20 is configured to space the first connector pin 16 at a suitable location for connection to the socket. The pin portion 46 of the first connector pin 16 may include a plating of a conductive material that can withstand sterilization in an autoclave and is suitable for contact with human tissue, such as nickel. The sleeve portion 48 is typically hollow or tubular and is fastened to the terminal portion 42 the inner conductor 20 any suitable manner, such as by crimping, welding, soldering, or in any other manner known in the art.

The second terminal pin 18 is electrically coupled to a terminal portion 50 of the outer conductor 22. The second terminal pin 18 is formed from a single piece of a suitable conductive material, such as brass, as is known in the art. The pin includes a pin portion 52 and a sleeve portion 54. The pin portion 52 is solid and extends from the housing 12 for a distance suitable for connection to the socket of the electrosurgical generator. The pin portion 52 is bent at first and second bends 56, 58 to form an offset 60 from the longitudinal axis 24 of the housing 12. The offset 60 is configured to space the pin portion 52 at a suitable location for connection to the socket. The sleeve portion 54 of the second connector pin 18 is arcuate in cross-section and typically extends in a circular arc for greater than 180°. The sleeve portion 54 is fastened to the terminal portion 50 of the outer conductor 22 in any suitable manner, such as by crimping, welding, soldering, or in any other manner known in the art.

Figure 8A:
FIGS. 8A, 8B, 8C, and 8D illustrate steps in the manufacture of the second connector pin of FIG. 4.
Figure 8B:
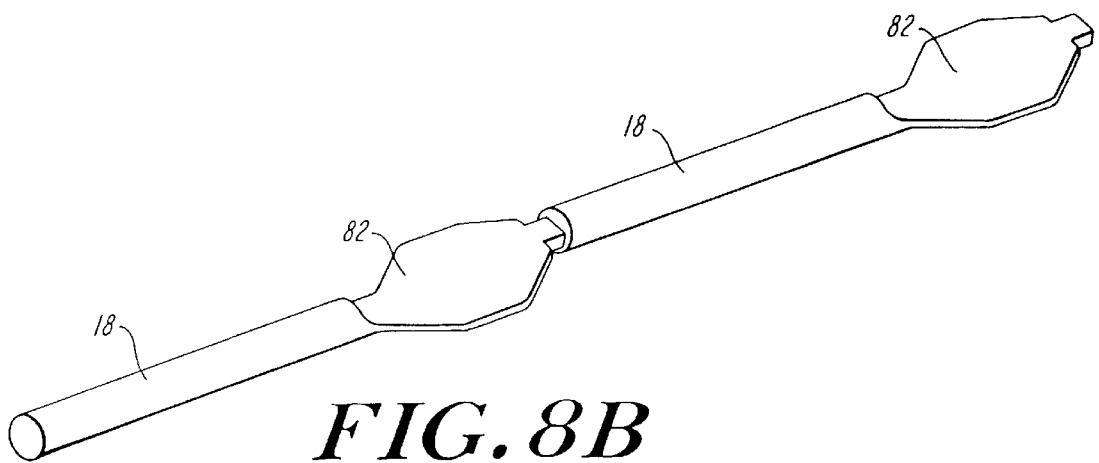
Figure 8C:
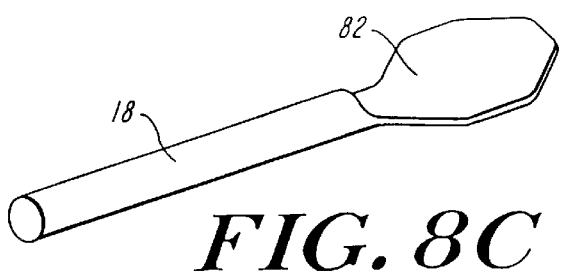
Figure 8D:
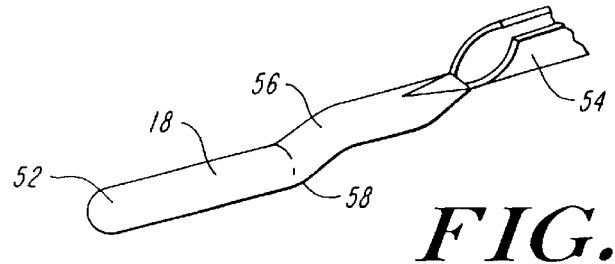

Referring to FIG. 8A, the second connector pin 18 is formed from a single piece of round wire 80 having a diameter sufficient to withstand the forming process. For example, a coiled brass wire, type 70/30, annealed and having a diameter of at least 0.073 inch has been found to be suitable. The wire is fed into a multi-slide machine which first straightens the wire. The multi-slide machine also coins, trims, and preforms the pin to have a flattened section 82. See FIG. 8B. The wire is cut to length to form an appropriate number of pins. See FIG. 8C. The flat portion is then formed to provide a circular arc having a diameter sized to fit around the outer conductor to form the sleeve portion 54, and the solid portion 52 is bent at 56 and 58 to form the offset 60 therein. See FIG. 8D. The part is stripped from the machine and plated with a suitable conductive material, such as bright nickel.

In assembly, the inner conductor 20 is covered with the insulating material 28 and cut to the appropriate length. The terminal portion 42 of the inner conductor 20 is left uninsulated, as by not applying the insulating material thereto or by removing the insulating material therefrom after application. The inner conductor 20 is bent to form the offset 38 therein. The inner conductor 20 is then placed inside the outer conductor 22, which has also been cut to the appropriate length. The sleeve portions 48, 54 of the first and second connector pins 16, 18 are placed over the inner conductor 20 and the outer conductor 22 respectively and electrically coupled thereto, thereby fastening the pins to the conductors. The assemblage of the coaxial conductor and the connector pins is placed in an insert mold for molding the housing 12 around the assemblage, leaving the tips of the coaxial conductor and the connector pins exposed. The housing 12 is formed from any suitable insulating thermoplastic material. After a sufficient cure time, the coagulator is removed from the mold.

Manufacture of the coagulator with offset connector pin according to the present invention is advantageous in that it results in a stronger electrical connection between the pin and the conductor and also eliminates several production operations that are required for the manufacture of coagulators such as shown in U.S. Pat. No. 5,089,002. In particular, the eliminated operations are bending the outer conductor, grinding an opening in the bent or offset portion of the connector through which an insulated wire passes, and crimping the tube to prevent the internal insulated wire from moving.

The coagulator of the present invention is particularly suitable for multiple uses with sterilization between uses, although it may be made to be disposable if desired. For reusable coagulators, the materials are chosen to withstand the heat of sterilization in an autoclave.

The invention is not to be limited by what has been particularly shown and described, except as indicated by the appended claims.

I claim:

1. A bipolar coaxial coagulator comprising:

an insulative housing comprising a single, unitary body extending along a longitudinal axis from a tip to a connector end;

a coaxial conductor disposed within the insulative housing along the longitudinal axis of the housing, the coaxial conductor comprising an inner conductor, an outer conductor coaxial with the inner conductor, and an insulating material concentrically disposed between the inner conductor and the outer conductor, the coaxial conductor protruding from the tip of the housing, the inner conductor including a terminal portion protruding from the outer conductor within the connector end of the housing, the terminal portion including an offset therein to space the terminal portion from the longitudinal axis;

a single-piece, first connector pin including a sleeve portion electrically coupled to the terminal portion of the inner conductor within the connector end of the housing, the first connector pin including a pin portion protruding from the connector end of the housing; and a single-piece, second connector pin including a sleeve portion electrically coupled to the outer conductor within the connector end of the housing along the longitudinal axis of the housing, the second connector including a second pin portion including an offset therein to space the second pin portion from the longitudinal axis and from the first connector pin.

2. The bipolar coaxial coagulator of claim 1, wherein the second pin portion includes first and second bends therein to form the offset.

3. The bipolar coaxial coagulator of claim 1, wherein, in the second connector pin, the second pin portion is offset in a direction away from the sleeve portion.

4. The bipolar coaxial coagulator of claim 1, wherein the first connector pin and the second connector pin are formed from brass.

5. The bipolar coaxial coagulator of claim 1, wherein the first connector pin and the second connector pin are plated with an electrically conductive material.

6. The bipolar coaxial coagulator of claim 1, wherein the electrically conductive material comprises nickel.

7. The bipolar coaxial coagulator of claim 1, wherein the housing is comprised of a thermoplastic material.

8. The bipolar coaxial coagulator of claim 1, wherein the inner conductor and the outer conductor are comprised of stainless steel or pure nickel.

9. The bipolar coaxial coagulator of claim 1, wherein the first and second connector pins are spaced to connect to a socket of an electrosurgical generator.

* * * * *